United States Patent [19]
Grandpierre et al.

[11] Patent Number: 4,756,194
[45] Date of Patent: Jul. 12, 1988

[54] METHOD AND SYSTEM FOR CONTROLLING CRACKS IN LOADED STRUCTURES

[75] Inventors: Loïc Grandpierre, Toulouse; Augustin Moliné, Pibrac, both of France

[73] Assignee: Aerospatiale Societe Nationale Industrielle, Paris, France

[21] Appl. No.: 940,906

[22] Filed: Dec. 11, 1986

[30] Foreign Application Priority Data

Dec. 16, 1985 [FR] France ............................ 85 18601

[51] Int. Cl.$^4$ .......................................... G01N 19/08
[52] U.S. Cl. ..................................................... 73/799
[58] Field of Search .................................... 73/799, 802

[56] References Cited

U.S. PATENT DOCUMENTS

| | | | |
|---|---|---|---|
| 3,596,269 | 7/1971 | Laska | 73/799 |
| 4,107,980 | 8/1978 | Crane et al. | 73/799 |
| 4,175,447 | 11/1979 | Fukuhara | 73/799 |
| 4,304,135 | 12/1981 | Peterson et al. | 73/799 |

FOREIGN PATENT DOCUMENTS

2066964 7/1981 United Kingdom ................ 73/799

OTHER PUBLICATIONS

Deans et al., "A Simple and Sensitive Method of Monitoring Crack and Load in Compact Fracture Mechanics Specimens Using Strain Gages", J. Test. & Eval. (USA), vol. 7, No. 3 (May 1979).

Schijve et al., "A Specimen for a Constant Stress Intensity Factor", Engineering Fracture Mechanics, vol. 9, No. 2, pp. 331-340, 1977.

Primary Examiner—Stewart J. Levy
Assistant Examiner—Robert R. Raevis
Attorney, Agent, or Firm—Marshall, O'Toole, Gerstein, Murray & Bicknell

[57] ABSTRACT

Method and system for monitoring cracks liable to appear and/or to grow in one point of a loaded structure. According to the invention, a theoretical increase of the length of the crack is cumulatively calculated, as and when the stresses are exerted, from said initial length, so as to determine an instant theoretical crack length; said instant theoretical length is permanently compared to said maximum acceptable length, and said point is inspected as soon as said instant theoretical length reaches said maximum acceptable length.

8 Claims, 2 Drawing Sheets

METHOD AND SYSTEM FOR CONTROLLING CRACKS IN LOADED STRUCTURES

BACKGROUND OF THE INVENTION

The present invention relates to a method and system for monitoring the growth of cracks liable to occur in loaded structures.

It is known that, in structures undergoing strong stresses such as aircrafts, ships, vehicles, platforms and pipes structures, cracks are liable to appear and/or grow in certain critical points. For example, such critical points correspond to the position of rivets joining up metal plates constituting the skin of the fuselage of an aircraft, in which plates risks of cracks may occur around the edges of the holes receiving said rivets.

For obvious reasons of security, said critical points need to be inspected periodically, in order to check that any cracks occurring do not affect too much the mechanical strength of the structure. But for reasons of economy, maintenance should be adapted to the use of the structure and inspections and repairs should only be carried out if a damage of sufficient importance is expected to have occurred. Indeed, in composite or metallic parts which are subjected to a complex stress system when in use, damages due to fatigue can appear at very variable time, depending on how the said parts have been used.

In order to follow the propagation of cracks, it is already known to use, especially in laboratory tests, devices such as:
  rip links, namely wires or fiber glass yarns which are bonded as close as possible to the expected damage, perpendicularly to the crack; these are wires which break as the crack gradually grows.
  indestructible control sensors such as:
    supersonic, eddy current or other type of sensors which are placed close to the critical points. As soon as the fault reaches the detectability level, namely the size which can be detected by the method, said fault is identified by the device;
    sound, electric or optical probes for determining the appearance of a fatigue crack.

Such devices are generally expensive and can only perform a good monitoring operation from a very limited and accessible zone. They also require a very particular maintenance.

SUMMARY OF THE INVENTION

It is the object of the present invention to overcome these disadvantages and to propose a system for monitoring the propagation of cracks permitting the use of strong and reliable sensors, such as stress gauges, without the need of any particular human intervention. Moreover, the system according to the invention, by its structure, although it can be used separately, is particularly adapted to be combined with a system for monitoring the fatigue of the elements of said structure as a function of said stresses, with a view to forming a complete system for monitoring, during service, the tolerance of said structure towards damages.

To this end the method according to the invention for monitoring the possible appearance and/or growth of a crack in one point of a structure subjected to stresses, is noteworthy in that it consists in:

(a) determining a maximum acceptable crack length, beyond which the mechanical strength of said structure in said point risks being too low for the structure to fulfill the function for which it was built;

(b) determining an initial crack length;

(c) permanently measuring the stresses to which said point of the structure is subjected;

(d) cumulatively computing, as and when said stresses are applied, a theoretical increase of the length of said crack from said initial length, so as to determine an instant theoretical length of the crack;

(e) permanently comparing said theoretical length to said maximum acceptable length; and (f) inspecting said point as soon as said instant theoretical length reaches said maximum tolerable length The choice of the inital crack length may result from an actual measurement of said length, for example with a supersonic sensor or the like, particularly when the crack is initiated and detectable before the present invention is carried out. However, in the particular case where there is no crack (such as a new structure), or where the crack is not detectable with the conventional sensors, said initial crack length is given a set or arbitrary value, determined by regulations, experience or caution. For example, if the invention is applied to a structure just manufactured (and which therefore should not have any cracks) in which cracks are liable to develop from a hole receiving assembly means, such as rivets, the value selected for the initial crack length may be the radial width of the edge of said hole which is covered by the head of said assembling means; thus we place ourselves under the careful, although pessimistic assumption that a crack already exists and that the length of that crack has the maximum value that a non-visually detectable crack can have (non-detectable crack because hidden by said head of the assembling means).

The stresses to which the monitored point of structure is subjected can be measured by means of strain gauges of the conventional type, mounted for example in a Wheatstone bridge. Said gauges are, when said point is accessible, joined to said structure, for example by adhesive bonding, in the direct vicinity of this point. On the contrary, when said point is inaccessible, it is advantageous to place said gauges in an accessible point, reacting to the same type of stresses as the associated accessible point, so that, as far as the measured stresses are concerned, said accessible point is representative of the inaccessible point. In this last case, transfer functions have been established, from a detailed analysis corroborated by experience, which functions enable a correlation between the stresses at said inacessible point and the stresses at said accessible point.

The maximum acceptable crack length is readily determined by computation, taking into account the specifications which the structure has to follow.

During the inspection specified under (f), several cases may arise:

(1) no crack can be detected: in this case, operations (b) to (f) are repeated with the same initial crack length;

(2) a crack can be detected, but its length is less than said acceptable length: in this case, operations (b) to (f) are repeated, taking as initial crack length the actual measured length of said crack;

(3) a crack can be detected, but its length is more than said acceptable length: in this case a repair of the corresponding point of the structure is made, or the structure is scrapped.

Thus, in the case of a structure under control since it has left the manufacturing plant, the method according to the invention advantageously consists in:

(a) determining a maximum acceptable crack length beyond which the mechanical strength of the structure, at said point, risks being too low for said structure to fulfill the function for which it was built;

(b) attributing a set initial length to any crack that may be present at said point at the end of the structure manufacturing process;

(g) performing operations (c) to (f) with said set initial length;

(h) repeating operation (g) as long as no detectable crack occurs; and (i) if necessary, performing operations (c) to (f) once or several times with one or more actual initial lengths measured during the inspection specified under (f).

Preferably, in the method according to the invention, the computing process consists in:

(j) during an operation (c) measuring the successive extremes of said stresses and the number N of successive cycles of variations thereof; and for each cycle of variation, determining the maximum value M and the minimum value m of said stresses C as well as the ratio $R=m/M$ and the difference $dC=M-m$;

(k) prior to an operation (d) establishing a table which gives, for the geometry of said structure, the value of ratio K/C in which K is the stress intensity factor, as a function of the crack length l; and (l) during an operaton (d), calculating:

(1.1) the variation $dK=(K/C) \cdot dC$ (1.2) the theoretical speed dl/dN of crack growth as a function of the number N of cycles of stress variations with the help of an expression $dl/dN=F(R,dK)$ in which F(R,dK) is a function of the ratio $R=m/M$ and of the variation dK of the stress intensity factor;

(1.3) by integrating the theoretical speed dl/dN, the theoretical increase of the length of the crack;

(1.4) by adding said length determined by the corresponding operation (b) and said theoretical increase obtained under (1.3), the instant theoretical length of the crack.

Advantageously, the function F(R,dK) specified under (1.2) is of the type:

$$F=c[(a+bR)dK]^m$$

in which a, b, c are constants.

For carrying out the method according to the invention, there is provided a system comprising at least one electronic computer.

BRIEF DESCRIPTION OF THE DRAWINGS

The invention will be more readily understood on reading the following description with reference to the accompanying drawings, in which.

DETAILED DESCRPTION OF THE INVENTION

Figure 1:
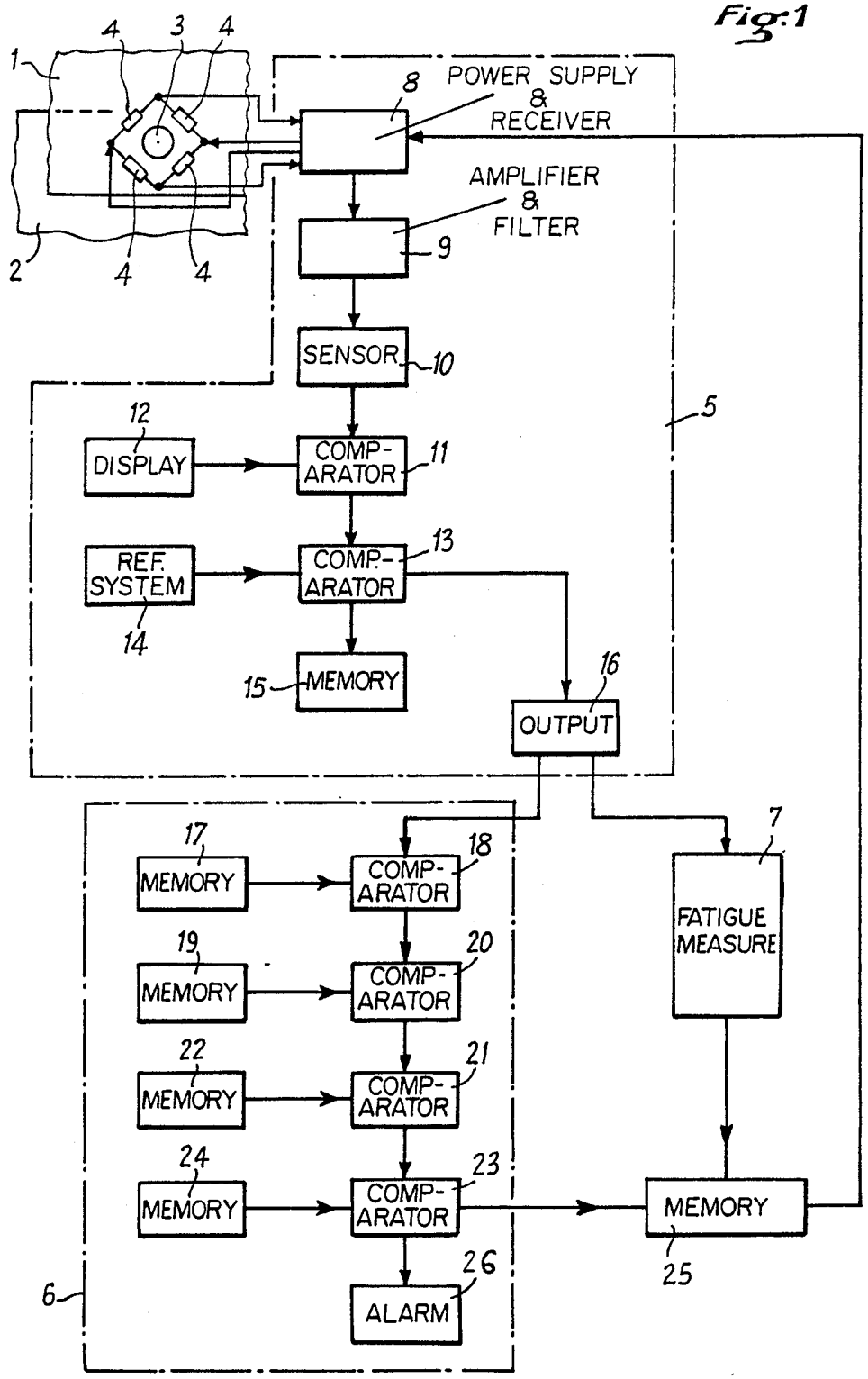
FIG. 1 is a block diagram of one embodiment of the system according to the invention.

The system according to the invention, illustrated as a block diagram in FIG. 1, is for example intended for monitoring the damages suffered by the outer skin of an aircraft, as regards crack growth and fatigue. In this case, said system is advantageously produced in compact form in order to be taken on board the aircraft, and to communicate appropriately to the crew or maintenance staff the results of its computations.

FIG. 1 succinctly represents two metal plates 1 and 2 from the skin of the fuselage, of which the edges overlap and are assembled together by rivets 3.

Close to the rivets 3 to be monitored (or close to accessible rivets 3 representative of rivets 3 to be monitored but inaccessible), a set of strain gauges is fixed on the skin, the gauges being shown in a Wheatstone bridge.

The system according to the invention comprises a unit 5 for detecting and measuring the stresses suffered by the fuselage skin close to the monitored rivets 3, a unit 6 for monitoring the growth of any cracks that may appear on said skin close to said rivets, and a unit 7 for measuring the fatigue of the skin.

The detecting and measuring unit 5 comprises a device 8 for the electric supply of one or more bridges of gauges 4, as well as for the acquisition of signals issued therefrom.

Figure 2:
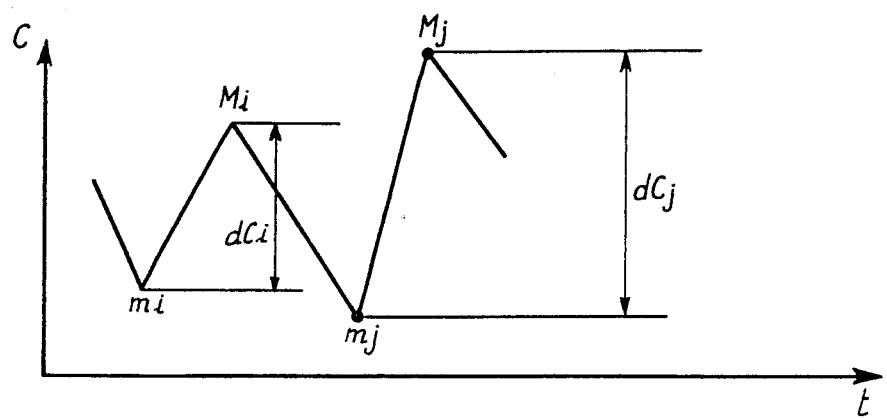
FIGS. 2 and 3 illustrate how the system shown in FIG. 1 works.

Said signals, representing stresses C exerted on said skin where the said bridges of gauges 4 are situated, may vary as a function of the time t which goes through a succession of extremes (maximum ($M_i,M_j$) and minimum ($m_i,m_j$)) such as diagrammatically illustrated in FIG. 2. Said signals are applied to a processing device 9 in order to be filtered and amplified therein in the normal way.

The processed signal, issued from device 9, are transmitted to a sensor 10. Said sensor detects the extremes, $m_i$, $M_i$, and works out, for every cycle of variations of the stresses C, the differences $dC_i=M_i-m_i$, as well as the ratios $R_i=m_i/M_i$ and records said cycles.

In order not to use unnecessarily the computing capacity of the system according to the invention, said system is provided with a comparator 11 which makes it possible to compare each $dC_i$ with a minimum threshold $dC_m$ which is delivered by a display device 12 and below which all differences $dC_i$ are eliminated in order not to be taken into account.

On the contrary, for every $dC_i$ above said minimum threshold $dC_m$, the corresponding maximum $M_i$ is addressed to another comparator 13, in order to be compared with an acceptable maximum $M_a$ delivered by a reference system 14.

If the maximum $M_i$ reaches or exceeds the maximum acceptable value $M_a$, said maximum $M_i$, as well as its time of appearance are recorded in a memory 15, for subsequent analysis.

At its output 16, unit 5 supplies the ratios $R_i$, the differences $dC_i$ and the number N of detected and retained stress cycles.

These quantities are supplied both to unit 6 and to unit 7.

Figure 3:
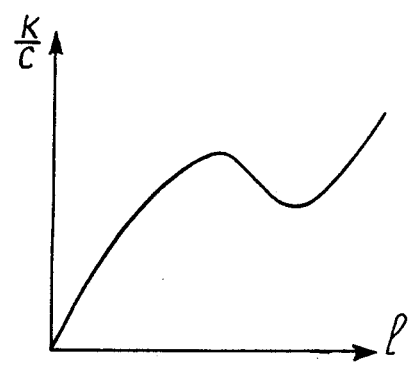

Unit 6 which is particularly intended for monitoring cracks liable to appear close to the rivets 3, comprises a memory 17 in which is stored, in the form of a table, a curve (such as that shown in FIG. 3) giving the stress intensity factor K/C as a function of the length l of a crack.

Such curve is determined either by a preliminary detailed calculation, or by the assessment of a damage which has occurred during tests or during operation.

By way of example, it has been found that the function:

$$\frac{K}{C} = \sqrt{\pi \times 1}$$

is representative of the variations of the stress intensity factor for plates 1 and 2 made from an alloy 2124 T T 351, and for a range of lengths varying between 5 and 100 mm. In this case, the table stored in the memory is as follows:

| 1 (mm) | K/C ($\sqrt{mm}$) |
|---|---|
| 5 | 3.95 |
| 10 | 5.60 |
| 15 | 6.86 |
| 20 | 7.93 |
| 25 | 8.86 |
| 30 | 9.71 |
| 35 | 10.49 |
| 40 | 11.21 |
| 45 | 11.89 |
| 50 | 12.53 |
| 55 | 13.14 |
| 60 | 13.73 |
| 65 | 14.29 |
| 70 | 14.83 |
| 75 | 15.35 |
| 80 | 15.85 |
| 85 | 16.34 |
| 90 | 16.81 |
| 95 | 17.28 |
| 100 | 17.72 |

The computing device 18 of unit 6 receiving both the stress variation dC (in the form of the various dCi) from output 16 and the table K/C from the memory 17 is therefore capable of calculating the stress intensity variation $dK = (K/C).dC$.

Moreover, unit 6 comprises another memory 19, in which is stored, in the form of a table, a function F(R,dK) representative of the theoretical speed dl/dN of growth of the cracks.

Such function F(R,dK) can be selected for example like that of ELBER, of the type:

$$dl/dN = c[(a+bR)dK]^m$$

in which a, b, c and m are constants.

For example, for the alloy 2124 T 351 mentioned hereinafter in a thickness of 6 mm, said constants take on the following values:
a=0.184
b−0.133
c=7.10$^{-7}$
m=3.2 in cases where the stresses C are expressed in hbars.

Thereafter, the computing device 20, receiving the coefficients a, b, c and m (from the memory 19) as well as R and dK (from the computing device 18), can work out the crack theoretical growth speed as a function of the stresses measured by gauges 4.

In integrator 21, said theoretical growth speed is integrated in order to furnish a theoretical increase of the crack length. To this theoretical length increase is added an initial crack length stored in an adjustable memory 22, so that the integrator 21 delivers in output the theoretical crack length. Said length is transmitted to a comparator 23 which, on the other hand, receives a maximum acceptable crack length stored in a memory 24.

In the case where the theoretical crack length is at least equal to said maximum acceptable length, the comparator 23 actuates an alarm 26.

In the case where the theoretical crack length is less than the maximum acceptable length, it is stored in a memory 25 which also receives the results from the fatigue measuring unit 7 and which is linked with device 8.

Understandably, the various computing devices, comparators, memories, etc... mentioned hereinabove, can be part of an electronic computer.

Thanks to the invention, the system obtained presents many advantages.

Indeed, it can be integrated in a system on board an aircraft in order to monitor the structure of said aircraft, and it can use microprocessors such as of latest technology, which further permits, with a sophisticated software, the use of transfer functions, as well as the recognition of the cause of an anomaly in the signal. It can carry out all the computations in real time during the processing operation, without the need for any kind of human intervention. Indeed, this system realizes, with the help of sophisticated computing patterns, validated by tests, the computing of the damage caused by fatigue, of the growth of an initial damage up to the detectable length, and of the growth of a detectable damage up to a critical length. It can also memorize situation parameters in cases where a stress threshold has been exceeded, this permitting, thanks to a detailed analysis of the stresses exerted on the structure, the memorizing of less information.

Calculations of the growth, from a detectable or hypothetical crack, take into account the fact that, after each inspection, the crack length may be re-initialized to the detectable length by the provided inspection means.

The fatigue reckoning unit 7 may be of conventional type, such as calculating the fatigue from worked out data, for example GOODMAN sheets adapted to the material and to the geometry of the monitored points.

We claim:

1. Method for monitoring a crack in one region of a loaded structure, said method comprising the steps of:
    (a) establishing a maximum acceptable crack length beyond which the mechanical strength of said structure in said region would be too low for said structure to fulfill its intended function;
    (b) determining an initial crack length l;
    (c) continuously measuring the stresses C to which said region of the structure is subjected;
    (d) calculating, as and when said stresses are applied, a theoretical increase in the length of said crack from said initial length, so as to determine an instantaneous theoretical length of the crack;
    (e) continuously comparing said theoretical length to said maximum acceptable length;
    (f) inspecting said region as soon as said theoretical length reaches said maximum acceptable length;
    step (c) comprising measuring the successive extremes of said stresses and the number N of successive cycles of variations thereof, and for each cycle of variation, determining the maximum M and minimum m values of said stresses C, as well as the ratio $R=m/M$ and the difference $dC=M-m$;

(g) establishing prior to step (d), a table which gives, for the geometry of said structure, the value of ratio K/C, in which K is the stress intensity factor, as a function of the crack length l;

step (d) comprising:

(1) calculating the variation dK of the stress intensity factor from the expression:

$$dk=(K/C)\cdot dC;$$

(2) calculating the theoretical speed dl/dN of crack growth as a function of the number N of cycles of variations of the stresses from the expression $dl/dN=F(R,dK)$ in which $F(R,dK)$ is a function of the ratio $R=m/M$ and of the variation dK of the stress intensity factor;

(3) calculating the theoretical increase of the crack length by integration of the theoretical speed dl/dN; and (4) calculating the instantaneous theoretical crack length by adding said initial length determined under the corresponding step (b) and said theoretical increase as previously calculated.

2. Method as claimed in claim 1, wherein said initial crack length is determined by measurements.

3. Method as claimed in claim 1, wherein said initial crack length is preset.

4. Method as claimed in claim 1, wherein if no crack can be detected during the inspections conducted under step (f), steps (b) to (f) are repeated with the same initial crack length.

5. Method as claimed in claim 1, wherein, if a crack can be detected during the inspection specified under step (f) and if the length of said crack is less than said maximum acceptable length, steps (b) to (f) are repeated, using as said initial crack length, an actual measured length of the crack.

6. Method as claimed in claim 1, wherein, if a crack can be detected during the inspection specified under step (f) and if its length is more than said maximum acceptable length, said region of the structure is repaired or said structure is scrapped.

7. Method as claimed in claim 1 wherein:

in step (b), said initial crack length is determined by attributing a set initial length to any crack that may be present in said region;

steps (c) to (f) are performed with said set initial length; and steps (c) to (f) are repeated as long as no detectable crack occurs; and if necessary, steps (c) to (f) are performed one or more times with one or more initial crack lengths as measured during inspection step (f).

8. Method as claimed in claim 1 wherein said function $F(R,dK)$ is of the type:

$F=c((a+bR)dK)^n$ in which a, b, c and n are constants.

* * * * *